United States Patent [19]

Wittkampf et al.

[11] Patent Number: 4,515,161

[45] Date of Patent: May 7, 1985

[54] DUAL CHAMBER PACEMAKER SYSTEM WITH V-A TIME MEASUREMENT APPARATUS AND METHOD

[75] Inventors: Frederik H. M. Wittkampf, Brummen; Willem Boute, Doesburg, both of Netherlands

[73] Assignee: Vitafin N.V., Curacao, Netherlands

[21] Appl. No.: 569,669

[22] Filed: Jan. 10, 1984

[51] Int. Cl.³ .............................................. A61N 1/36
[52] U.S. Cl. .............................................. 128/419 PG
[58] Field of Search .................. 128/419 PG, 419 PT

[56] References Cited

U.S. PATENT DOCUMENTS

| | | | |
|---|---|---|---|
| 4,021,736 | 5/1977 | Walters et al. | 128/419 PT |
| 4,239,985 | 11/1980 | Hartlaub et al. | 128/419 PG |
| 4,312,355 | 1/1982 | Fonke | 128/419 PG |
| 4,452,248 | 6/1984 | Keller, Jr. | 128/419 PG |

Primary Examiner—William E. Kamm
Attorney, Agent, or Firm—Woodcock Washburn Kurtz Mackiewicz & Norris

[57] ABSTRACT

A dual chamber pacemaker having means for operating in different pacing modes, including dual chamber modes, contains the capability of switching into a fixed rate ventricular pacing mode and of sensing early atrial signals without affecting the ventricular pacing timing. The timing of a plurality of such sensed early atrial signals is analyzed to determine if they represent retrograde P waves and, if so, the indicated V-A conduction time. The pacemaker atrial refractory time is adjusted so that, during dual chamber operation, the atrial refractory time extends past the time of anticipated retrograde P waves, thereby optimizing the setting of the atrial refractory period for avoidance of pacemaker mediated tachycardia. Other pacing conditions may also be adjusted in response to the determined patient V-A time.

14 Claims, 5 Drawing Figures

DUAL CHAMBER PACEMAKER SYSTEM WITH V-A TIME MEASUREMENT APPARATUS AND METHOD

BACKGROUND OF THE INVENTION

This invention relates to dual chamber cardiac pacemakers and, more particularly, such pacemakers which have means for reprogramming of operating parameters, and particularly the atrial refractory period.

Dual chamber cardiac pacemakers have come into increasing use in recent years. The advantages of dual chamber pacemakers over single chamber pacemakers, i.e., those that pace and/or sense only in the ventricle or the atrium, are known in the art and have been the subject of extensive literature. However, a recurring and longstanding problem with the dual chamber pacemakers is their vulnerability to pacemaker mediated tachycardia which is caused by sensing retrograde P waves and increasing pacing rate as a result thereof. As has been described in the literature, a patient's heart has a retrograde conduction path from the ventricle back to the atrium, even frequently in cases where there is no antegrade conduction. As a result, a delivered ventricular stimulus may be sensed by the atrial lead of a dual chamber pacemaker, and falsely recognized as a natural P wave. When this happens, the pacemaker timing is reset earlier than it should be, i.e, it is reset at the time of the sensed retrograde P wave instead of at the time of occurrence of the next naturally occurring P wave which would have come later. Thus, the succeeding ventricular stimulus is delivered sooner than otherwise, the cycle repeats, and the pacemaker rate goes dangerously high.

There has been a great deal of effort in the pacemaker industry to solve the problem of pacemaker induced tachycardia. Many of these efforts have resulted in the response of attempting to properly set the atrial refractory period, so that the pacemaker does not act upon a P wave which is sensed early and before the naturally occurring P wave is expected. Even in such systems, problems often result. For example, some dual chamber pacemakers attempt to limit the frequency of operation caused by naturally occurring high rate atrial signals, by stretching out the A-V delay, in what is called the Wenckebach mode of operation. As is known in the art, extending the A-V delay increases the vulnerability to retrograde P waves being sensed after time-out of the atrial refractory period. Basically, the problem is that the longer the atrial refractory period, the less is the chance of detecting natural P waves through a rate range that is anticipated; the shorter the atrial refractory period, the more the probability of sensing retrograde P waves. Thus, there may be a problem with setting the atrial refractory period either too long or too short, and this dilemma has plagued the industry.

One approach to the problem that has been embodied in a commercially available pacemaker system is to determine the V-A conduction time at the time when the pacemaker is being implanted, and to set the atrial refractory period so that it extends just safely beyond the time when the retrograde P wave should arrive in the atrium. Since the A-V delay is programmed, if the V-A conduction time is known, it can be determined when in the pacemaker cycle it should be safe to sense atrial signals with assurance that they are natural signals and not retrograde P waves. However, this is not a safe practice for the reason that a patient's V-A conduction time can change and generally does change with time. It is known that both the natural antegrade and retrograde conduction times will change, and frequently do change after pacemaker implantation. This being the case, the determination of retrograde V-A conduction time at the time of implant will have little practical value throughout much of the pacemaker lifetime.

Another known technique in the art is that of delivering a single early stimulus in the ventricle, the timing being designed to produce a retrograde P wave before the next expected natural P wave appears. Measurement of the time interval between the early ventricular stimulus and the following P wave should, if it is a retrograde P, give the V-A conduction time. However, such a "one-time" measurement is very unreliable. There is no assurance that a retrograde P has been detected, and indeed the physician would be uncertain as to whether the patient's heart even exhibited retrograde conduction at that time. Further, since conduction rate varies somewhat with pacing rate, there would be less than an optimal amount of information from which the physician could intelligently choose a refractory period.

There thus remains a substantial need in the industry for a means and method of non-invasively determining a patient's retrograde conduction time, so that the atrial refractory interval can be adjusted accordingly. It is recognized that atrial refractory period is a programmable parameter which, in many existing pacemaker systems can be programmed from external apparatus. This being the case, if a means for non-invasively determining the V-A conduction time can be found, the atrial refractory period can be optimally adjusted. Further, it would be desirable to have automatic means in an implanted pacemaker for determining the V-A conduction time and automatically adjusting the atrial refractory time or pacing mode accordingly.

SUMMARY OF THE INVENTION

In view of the above discussion, the pacemaker system and method of this invention provide a means and method for optimizing the setting of atrial refractory time in an implanted cardiac pacemaker.

It is an object of this invention to provide non-invasive means, and a method of using same, for reliably determining V-A conduction time of a patient who is being paced by an implanted pacemaker.

It is another object of this invention to provide means and a method for programming the atrial refractory period or pacing mode of an implanted dual chamber pacemaker as a function of determined V-A conduction time of the patient being paced.

Accordingly, this invention provides a method and means of programming operation of an implanted pacemaker so as to give an indication of the patient's V-A conduction time, and for setting the atrial refractory period of the pacemaker in response to the determined V-A conduction time, so as to minimize the probability of pacemaker mediated tachycardia due to retrograde P waves and maximize the sensing of natural atrial signals. The invention may be embodied through the means of external programming apparatus or may be embodied through fully automatic means within the implanted pacemaker. The pacemaker system is provided with means for going into a pacing mode where atrial signals are sensed but the ventricular pacing rate is maintained stable and is not responsive to sensed atrial signals. The time duration between ventricular stimuli and following sensed atrial signals is determined over a plurality of cycles; if it stays substantially constant, the sensed atrial signals are determined to be retrograde P waves, and the time duration corresponds to V-A conduction time. The pacemaker atrial refractory period, high rate limit or mode may then be adjusted automatically or by the physician.

DESCRIPTION OF THE PREFERRED EMBODIMENTS

Figure 2A:
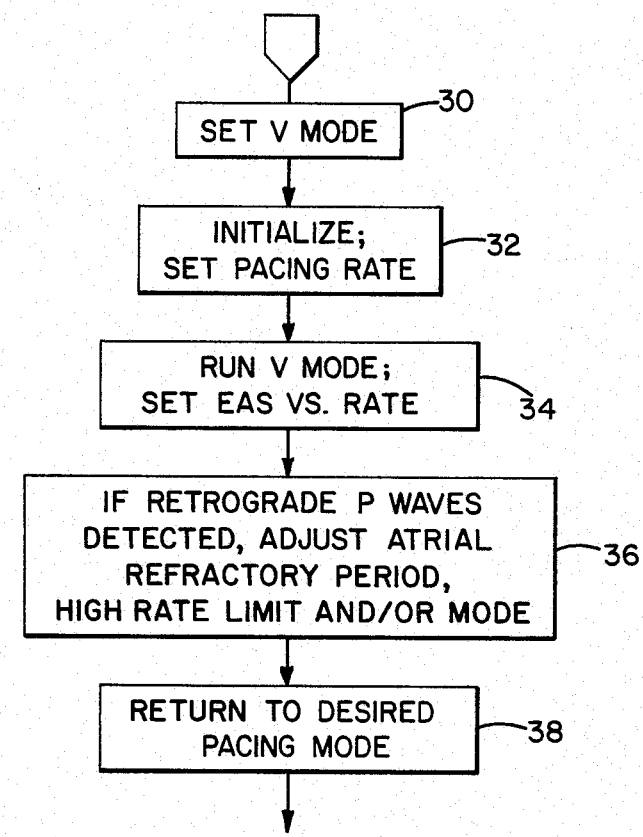
FIG. 2a is a flow diagram illustrating the primary steps of the method of this invention.
Figure 2B:
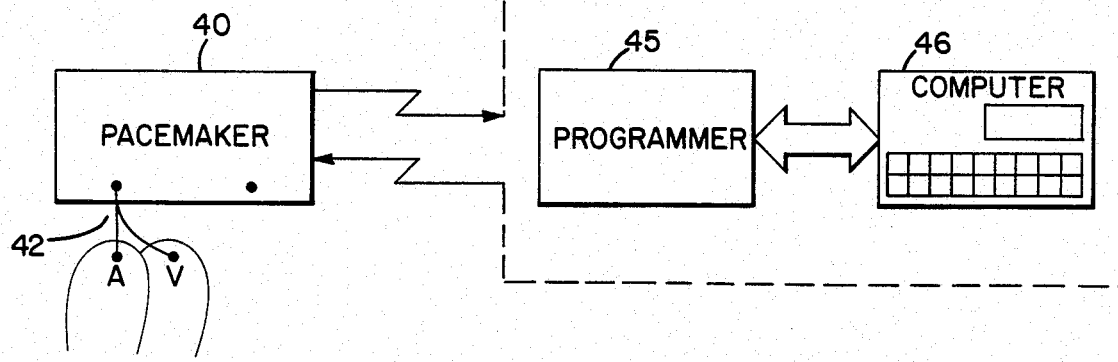
FIG. 2b is a block diagram illustrating the primary components of this invention for the external programmer embodiment.

The pacemaker used with this invention is a dual chamber pacemaker as illustrated at 40 in FIG. 2b, and is connected to the heart by a lead 42. It is preferably a multi-mode pacemaker, and can be used in a synchronous mode wherein a sensed natural atrial signal is used to time out a delivered ventricular stimulus after a predetermined A-V time delay. In the preferred embodiment of this invention, the pacemaker is a DDD type pacemaker and can be programmed to operate in any one of the known pacemaker modes, including single chamber operation. Of course, the retrograde P wave problem discussed above occurs only when operating in a mode wherein atrial signals are sensed and the pacemaker timing is responsive to the sensed atrial rate.

In normal dual chamber operation, where the pacing rate is determined by the atrial rate, it is not possible to reliably determine the patient's V-A conduction time by any direct measurement. However, we have observed that if the pacemaker is put into a fixed vetricular pacing mode, e.g., VAO mode, then in fact the conduction time can be determined if the pacemaker knows how to look for it. In order to make the V-A conduction time measureable, it is required that there be no atrial stimulation; that the atrial sensing does not trigger synchronous ventricular stimuli or recycling; and that there is stable ventricular stimulation over a plurality of cycles. Ventricular inhibition in the event of sensed natural V signals is safer and optional within this invention, although it renders the technique more complicated.

Figure 1:
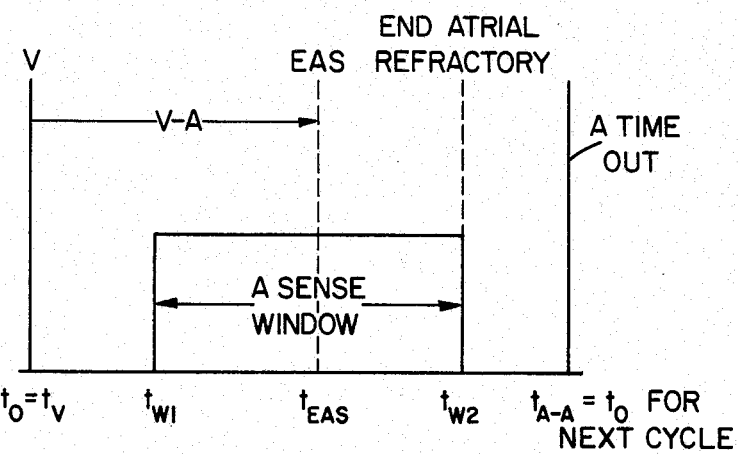
FIG. 1 is a timing diagram illustrating the method of this invention for determining a patient's V-A conduction time while the patient is being paced by an implanted pacemaker.

Referring to FIG. 1 there is illustrated a timing diagram which shows the means of determining the V-A conduction time. In the VAO mode, which is used by way of example, the fixed rate stimulus pulses are delivered to the ventricle, and sensing is done in the atrium only. As shown in FIG. 1, the start of the pacer's cycle is at $t_o$, which is when the ventricular stimulus is delivered. Following this, an atrial sense window is timed out between times $t_{W1}$ and $t_{W2}$. In this invention, the atrial sense window may, for example, occur from about 75 to 500 ms following the ventricular stimulus. It is necessary to blank atrial sensing during the V stimulus, and for approximately 75 ms after the V stimulus when a monopolar atrial lead is used.

During the atrial sense window, a sensed signal termed an early atrial signal (EAS) does not cause resetting of the pacemaker and the starting of a new cycle, but is simply recorded with respect to its time. The atrial refractory period is set to be equal to the pacing interval, or as shown may end a short time period before the pacing interval is timed-out at $t_{A-A}$, at which time the next pacing cycle starts. It is to be noted that by setting the pacing rate reasonably high, e.g., 120 bpm or more, there is little likelihood of sensing a natural P wave within the A sense window. Thus, a P wave sensed within the A sense window is deemed to be not natural, or an early atrial signal probably caused by retrograde conduction. Moreover, for reasons discussed below, if a natural P wave is sensed within the window, it is detectable as such and is not confused with a retrograde P wave. As seen from the timing diagram, measurement of $t_{EAS}$ corresponding to the time of the retrograde P wave gives a direct measurement of V-A conduction time.

The technique of this invention is established from the observation that if retrograde P wave conduction is taking place, and the A sense window is set at a time which excludes natural P waves, then the EAS is going to occur at a substantially constant time at each pacing cycle, since the V-A conduction time remains substantially constant over the short duration of the test. Thus, if it is observed that early atrial signals are occurring, and that they have substantially a constant timing, it can be concluded that the retrograde V-A conduction time is represented by $t_{EAS}$. On the other hand, if $t_{EAS}$ varies over successive cycles of fixed ventricular stimulation, then it is apparent that the sensed atrial signals are not retrograde. Since it is theoretically possible that there could be a natural atrial rate at the exact setting of the ventricular pacing rate, further certainty can be added by changing the pacing rate, and determining whether the time of the EAS remains the same. If a change in pacing rate does not effect $t_{EAS}$, then there is additional certainty that it represents retrograde P waves, such that the V-A conduction time can be determined accurately.

Referring now to FIG. 2a, there is shown a flow diagram illustrating the salient operating steps of this invention. First, the implanted pacemaker is set into a ventricular pacing mode, e.g. VAO or VAI, as illustrated at block 30. In a presently preferred embodiment, this is done through a programmer 45, operated by a computer 46, as illustrated in FIG. 2b. Reference is made to U.S. application Ser. No. 465,891, assigned to the same assignee, which sets forth a means of programming an implanted pacemaker 40 with an external programmer 45 used in conjunction with a computer such as an HP 85. Application Ser. No. 465,891 is incorporated by reference.

Alternately, the implanted pacemaker may be programmed to automatically switch to the fixed rate ventricular pacing mode. This can be done, for example, on a daily or weekly basis, by counting pacing intervals, and switching to the VAO or VAI mode for determining V-A time whenever a predetermined amount of time has elapsed.

Following setting the pacemaker into the V mode, at block 32 the pacer is initialized and the initial pacing rate is set. When operation of the invention is carried out using an external programmer, the operator determines an initial fixed pacing rate appropriate to insure the probability of avoiding sensing natural P waves within the A sense window. Next, at block 34 the pacemaker is programmed to run in the selected V mode, and measures the timing of the sensed early atrial signals. In the preferred embodiment, the timing is checked over a predetermined plurality of cycles, and at two or more different predetermined pacing rates. Since V-A conduction time can vary somewhat with pacing rate, variation of the "test" rate provides more data from which to accurately determine the appropriate refractory interval.

At block 36 of FIG. 2a, it is determined whether retrograde P waves have been in fact detected. This can be done by the operator, by scanning the measured V-A times and seeing if they are substantially constant. If the operator sees that the V-A period is substantially constant, it is then determined that the V-A interval represents a retrograde V-A conduction time. Similarly, for an automatic embodiment of this invention, an algorithm is incorporated in the microprocessor memory to perform a logical analysis of the variance of measured V-A, with a conclusion of retrograde or not retrograde as a function of the logical analysis. Such logical analysis can be performed by a state-of-the-art program, utilizing the microprocessor type pacemaker as disclosed in EPO Application No. 81108940.8, which is incorporated by reference. For example, the microprocessor can store successive measured V-A intervals and obtain an average, or mean value over a predetermined number of cycles, preferably but not necessarily successive cycles. The mean value is then compared to determine whether the variance is significant or insignificant, i.e., a variance within ±5–10% of mean may be deemed to be insignificant. If insignificant, the P waves are deemed to be due to retrograde conduction, and the overall mean value is taken as the V-A conduction time. Additionally, mean values for each of a plurality of ventricular pacing rates may be determined.

After the retrograde conduction time has been determined, the atrial refractory rate is selected accordingly. For example, if the mean retrograde conduction time is determined to be 250 ms, the atrial refractory period is set to terminate more than 250 ms following delivery of the ventricular stimulus (time-out of the A-V delay). Alternately, or in addition, a different high pacing rate limit may be set. After the atrial refractory period has been adjusted at block 36, the pacemaker goes out of the special V mode and returns to the desired pacing mode, as illustrated at block 38 of FIG. 2a. This may involve returning to a dual chamber mode, or a decision may be made based upon the V-A time to go into a single chamber mode of pacing.

Figure 3A:
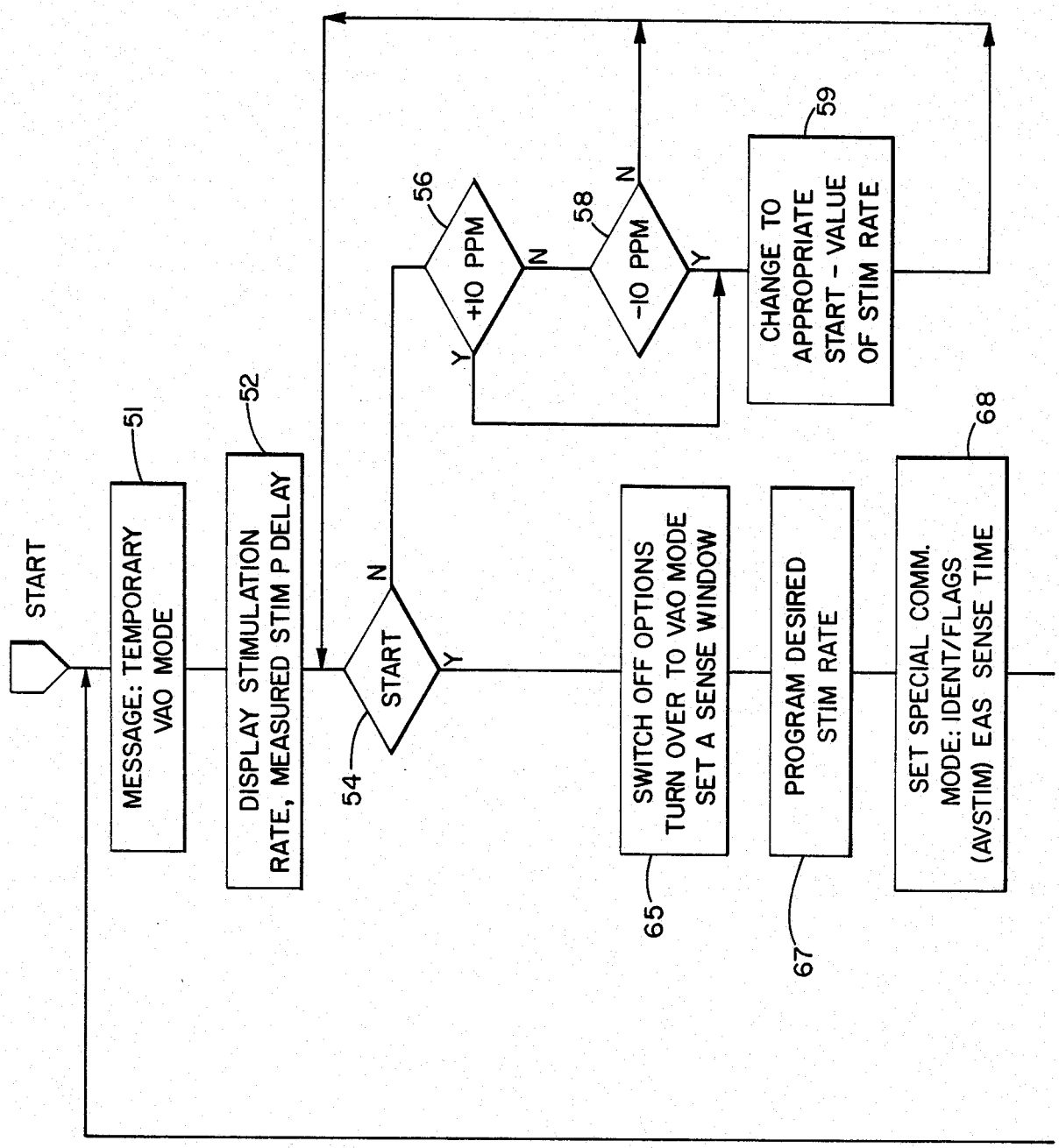
FIGS. 3a and 3b combined present a flow diagram of a computer routine, used in apparatus external to the implanted pacemaker, for carrying out the method of this invention.
Figure 3B:
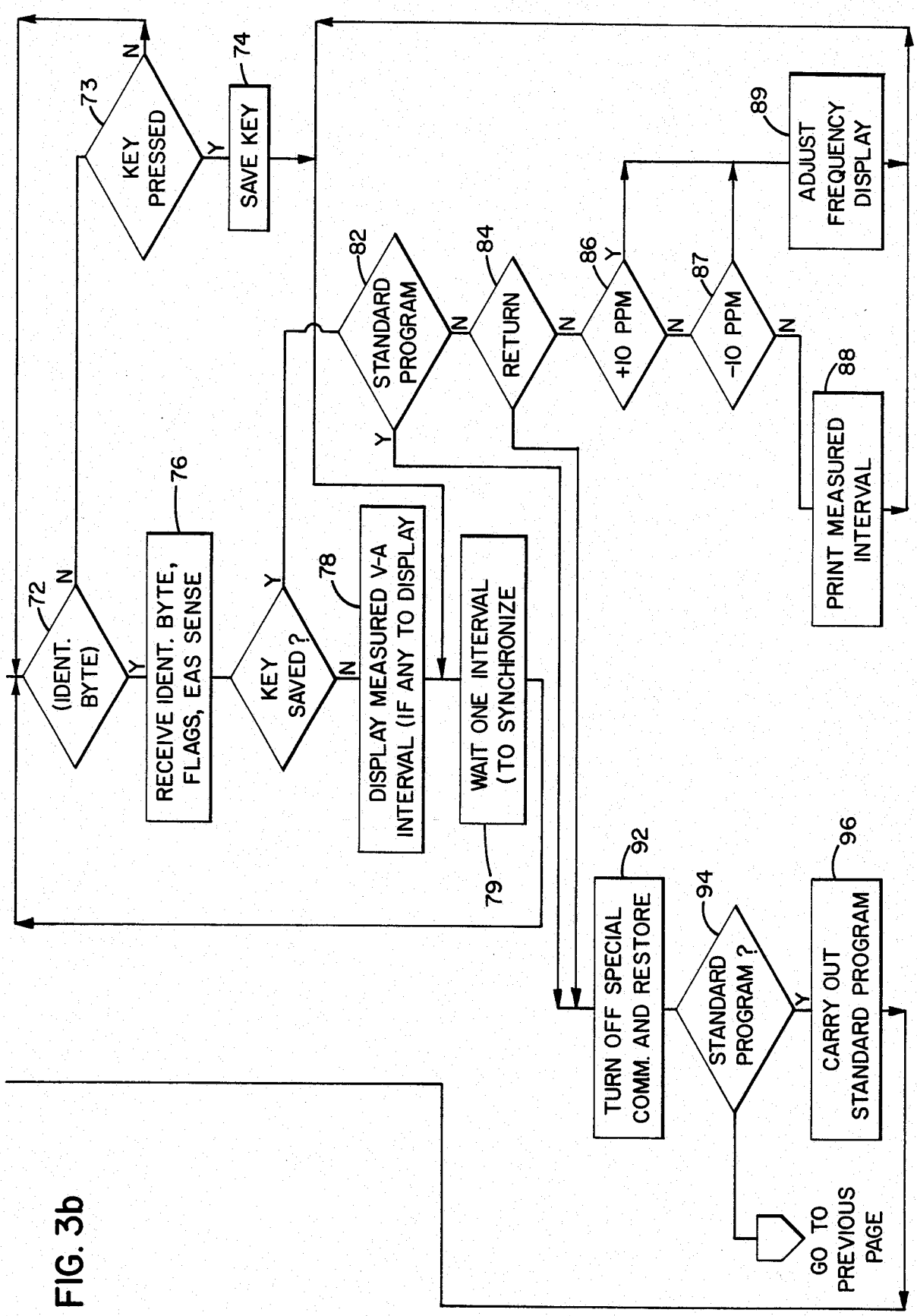

Referring now to FIGS. 3a and 3b, there is shown a block diagram of software for use in an external programming device, such as the HB 85 referred to in referenced EPO Application No. 81108940.8. At the start of the program, at block 51, a message is outputted, either by CRT display or printer, that the pacemaker is in the temporary VAO mode. The stimulation rate and measured V-A, or stimulus-P delay, derived from a prior loop of the program, is displayed at 52. At block 54, the program determines whether it is to start another sequence or first adjust the pacing rate. If the pacing rate is to be adjusted, it is determined at block 56 whether the pacing rate should be increased by incrementing 10 ppm, or at block 58 whether it should be decreased by 10 ppm. This decision is based upon inputted information from the operator. At block 59, the program changes the start value of the pacing rate to the selected start value, sets a start flag and goes back to decision block 54, whereupon the program continues to block 65.

At block 65, the programmer transmits data to the pacemaker which switches off other pacemaker options and turns the pacemaker over to VAO mode. The transmitted data also sets the refractory period equal to the selected pacing interval (A—A) less 50 ms, as illustrated in FIG. 1. At block 67, the pacemaker is programmed with the desired stimulus rate as set at block 59. At block 68, the external programmer sets the pacemaker into a special communication mode used to output data, and instructs it to output, each cycle, the required information. For the pacemaker as described in referenced application Ser. No. 465,891, the pacemaker periodically outputs an ident byte, appropriate flags, and the EAS time. The programmer then waits for a communication from the pacemaker.

At block 72, the programmer apparatus determines whether the communication is an IO interrupt (ident byte) from the pacemaker, indicating that a transmission is coming. Assuming that an indent byte has been received, the pacemaker next transmits to the programmer, and thence to the computer, the ident byte, flags, and EAS time. The apparatus 47 receives and processes the data at block 76 in a manner as explained in referenced application Ser. No. 465,891. The measured V-A interval is displayed, as shown at block 78, and at block 79 the programmer unit waits one pacing interval to synchronize and then loops back to block 72 to receive another ident byte and repeat the process. Thus, as long as the program loops through the routine between blocks 72 and 79, the programmer apparatus provides a series of measured V-A interval times.

When the operator wants to change the stimulation rate, he presses a key which causes a transmission to the pacemaker, which responds during the next cycle with a byte other than an ident byte. Thus, during the next cycle the program branches from block 72 to blocks 73, 74. The computer then gets out of the subloop at block 77, and at block 82 determines whether the same standard program is to be repeated. If yes, the program branches to block 92, turns off the special communications mode and restores, and then proceeds past block 94 to block 96 where it loops back to restart the temporary VAO mode. If the VAO mode is not to be run again with the same fixed rate setting, the programmer apparatus determines at block 84 whether it is to return to normal operation. If yes, the program passes through blocks 92 and 94, and returns to normal operation. If no return is called for, the program determines at blocks 86 and 87 whether the pacing rate is to be adjusted plus or minus 10 ppm. If there is no adjustment, the measured intervals are printed and the program loops back to block 79 and repeats. If there is a frequency adjustment called for, it is made at block 89, before looping back to run the program again.

At the conclusion of the temporary VAO mode of operation, the operator is presented with a list of measured V-A intervals corresponding to each of the different pacing rates utilized. From this it can be accurately determined whether retrograde P waves have been sensed, and if so what the V-A conduction time is. After this, the operator-physician accurately programs the atrial refractory period to optimize the pacemaker performance, avoiding retrograde P waves and also maximizing sensing of natural P waves.

Although the preferred embodiment has been illustrated for a system utilizing external programmer means as indicated at 47, it is to be understood that the invention can be carried out automatically by an implanted pacemaker. The DPG pacemaker of the assignee of this invention comprises a microprocessor and built in memory, and is capable of being programmed in the manner of this invention to automatically conduct V-A tests and to adjust refractory interval or pacing mode in response to the measured V-A conduction time. Thus, referring back to FIG. 2A, the step illustrated at block 30 may be taken automatically after passage of a predetermined amount of time. Thereafter a prior programmed starting pacing rate would be set for the fixed rate pacing in the ventricular test mode. The pacemaker timer is then set to measure the time of occurrence of the atrial signal each cycle, and to generate a mean or average $t_{EAS}$. Such a mean value can be done on an accumulated basis, or can be calculated after a predetermined number of V-A intervals have been actually measured. Of course, if a ventricular inhibited mode of operation is used, which would allow the natural heartbeat to take over during the determination of V-A conduction time, then only measured conduction times following delivered ventricular stimuli would be counted and accumulated. Thereafter, a convenient algorithm may be employed for automatically determining a desired refractory interval, e.g. adding a predetermined number of milliseconds to the measured mean V-A conduction time, or alternately increasing the V-A conduction time by a certain percentage and utilizing that as the atrial refractory interval. Further by comparing the indicated atrial refractory interval with predetermined criteria, a determination can automatically be made as to whether it is safe to return to dual chamber pacing or whether some other indicated pacing mode is to be selected.

We claim:

1. In a dual chamber cardiac pacemaker, a method of determining patient V-A conduction time and setting the pacemaker atrial refractory period as a consequence thereof, comprising the following steps:
   (a) setting the patient's pacemaker to a ventricular pacing mode and delivering ventricular stimulus signals at a first stable pacing rate;
   (b) enabling atrial sensing during a predetermined A sense window of the pacing cycle;
   (c) measuring the timing of sensed atrial signals relative to delivered ventricular stimulus signals;
   (d) determining whether said timing is substantially stable, and determining V-A conduction time as a function of determined stable timing; and
   (e) setting said atrial refractory period as a function of said determined V-A time, and returning the pacemaker to a selected mode of dual chamber operation.

2. The method as described in claim 1, wherein said ventricular pacing mode comprises the cyclical step of delivering of said ventricular stimulus signals independently of said atrial sensing.

3. The method as described in claim 2, further comprising the step of blanking atrial sensing at about the time of each delivered ventricular stimulus.

4. The method as described in claim 1, further comprising delivering ventricular stimulus signals at least a second stable pacing rate and determining V-A conduction time at said second stable rate, and setting said atrial refractory period as a function of the determined V-A conduction times.

5. The method as described in claim 1, wherein the step of enabling sensing during said A sense window is performed by externally programming the pacemaker.

6. The method as described in claim 1, wherein the method is carried out automatically by an implanted pacemaker.

7. Dual chamber pacemaker system apparatus, having means for sensing and pacing in both the atrium and ventricle, and means for operating in a plurality of pacing modes, comprising means for switching pacemaker operation into a fixed rate ventricular pacing mode; means for sensing atrial signals during a predetermined sense window of the fixed rate pacing cycle; means for measuring the timing of early atrial signals sensed within said sense window in relation to the pacing cycle; means for determining as a function of said timing whether there is retrograde V-A conduction, and for determining the V-A time thereof; and means for resetting the atrial refractory period as a function of said determined V-A conduction time and returning to a selected dual chamber mode of operation.

8. The apparatus as described in claim 7, wherein said pacemaker is an implantable pacemaker, and comprising programming means for selecting said fixed pacing mode.

9. The apparatus as described in claim 7, comprising means for changing the fixed pacing rate and determining V-A conduction time corresponding to each said fixed rate.

10. A dual chamber pacemaker system, having means for pacing and sensing in both the ventricle and atrium, and means for selecting the mode of operation, characterized by:
   means for setting a fixed rate ventricular pacing mode;
   means for sensing a plurality of atrial signals during a time such that they are likely to be other than natural P waves;
   logic means for determining if said sensed atrial signals are retrograde P waves;
   V-A means responsive to said logic means for determining the patient V-A conduction time from the timing of said sensed atrial signals when they are retrograde P waves; and
   refractory means for setting the pacemaker atrial refractory period as a function of said determined V-A conduction time.

11. A method of determining patient V-A conduction time utilizing a programmable dual chamber pacemaker system, comprising:
   setting said pacemaker into a ventricular pacing mode for pacing the ventricle by delivering stimuli independent of atrial signals;
   enabling atrial sensing only during a predetermined sense window of the pacing cycle, and measuring the V-A times of atrial signals sensed during said window, said sense window being set to achieve blanking of atrial sensing at least during delivery of ventricular stimuli;
   determining when said measured V-A times are substantially stable over a plurality of pacer cycles, and determining a patient V-A time as a function of said stable times; and
   setting the atrial refractory period of said pacemaker system as a function of said determined V-A time.

12. An implantable dual chamber pacemaker system having means for pacing the patient in which it is implanted, comprising retrograde conduction means for determining the presence of retrograde conduction in said patient and for determining retrograde conduction time, and varying means for automatically varying an operating condition or parameter of said system in response to said determined retrograde conduction time.

13. The pacemaker system as described in claim 12, wherein said varying means varies the system atrial refractory period.

14. The pacemaker system as described in claim 12, wherein said varying means varies the pacing mode.

* * * * *